United States Patent
Griffin et al.

(10) Patent No.: US 7,018,346 B2
(45) Date of Patent: Mar. 28, 2006

(54) GUIDE WIRE WITH ADJUSTABLE FLEXIBILITY

(75) Inventors: Stephen Griffin, Sunnyvale, CA (US); Gregory E. Mirigian, Dublin, CA (US)

(73) Assignee: Scimed Life Systems, Inc., Maple Grove, MN (US)

(*) Notice: Subject to any disclaimer, the term of this patent is extended or adjusted under 35 U.S.C. 154(b) by 273 days.

(21) Appl. No.: 10/025,428

(22) Filed: Dec. 18, 2001

(65) Prior Publication Data

US 2003/0114776 A1 Jun. 19, 2003

(51) Int. Cl.
*A61B 5/00* (2006.01)
*A61M 20/00* (2006.01)

(52) U.S. Cl. .................................................. 600/585

(58) Field of Classification Search ................ 600/585, 600/433, 434, 435; 604/164.13, 170.01, 604/171; 606/28
See application file for complete search history.

(56) References Cited

U.S. PATENT DOCUMENTS

| | | | |
|---|---|---|---|
| 4,427,000 A | 1/1984 | Ueda | |
| 4,753,223 A | 6/1988 | Bremer | |
| 4,838,859 A | 6/1989 | Strassmann | |
| 4,930,494 A * | 6/1990 | Takehana et al. ........... 600/145 |
| 4,984,581 A | 1/1991 | Stice | |
| 5,009,655 A | 4/1991 | Daignault, Jr. et al. | |
| 5,025,799 A | 6/1991 | Wilson | |
| 5,055,101 A | 10/1991 | McCoy | |
| 5,090,956 A | 2/1992 | McCoy | |
| 5,143,085 A | 9/1992 | Wilson | |
| 5,203,772 A | 4/1993 | Hammerslag et al. | |
| 5,211,183 A | 5/1993 | Wilson | |
| 5,349,946 A | 9/1994 | McComb | |
| 5,449,369 A | 9/1995 | Imran | |
| 5,497,786 A | 3/1996 | Urick | |
| 5,531,685 A | 7/1996 | Hemmer et al. | |
| 5,662,621 A * | 9/1997 | Lafontaine ................... 604/528 |
| 5,800,500 A * | 9/1998 | Spelman et al. ............. 607/137 |
| 5,938,623 A | 8/1999 | Quiachon et al. | |
| 5,957,966 A | 9/1999 | Schroeppel et al. | |
| 6,059,815 A * | 5/2000 | Lee et al. .................... 606/209 |
| 6,076,609 A | 6/2000 | Job | |
| 6,533,752 B1 * | 3/2003 | Waram et al. ........... 604/95.05 |
| 2001/0039412 A1 | 11/2001 | Fariabi | |

FOREIGN PATENT DOCUMENTS

WO WO 9510321 4/1995

* cited by examiner

*Primary Examiner*—Max F. Hindenburg
*Assistant Examiner*—Jonathan Foreman
(74) *Attorney, Agent, or Firm*—Crompton, Seager & Tufte, LLC

(57) ABSTRACT

A guide wire with a distal portion having adjustable flexibility. The guide wire may include a distal polymeric member and a heat source. The heat source may be activated to cause the polymeric member to increase in temperature and increase in flexibility. The increase in flexibility of the distal portion of the guide wire enhances the ability of the guide wire to navigate tortuous vasculature to a target site. After the guide wire has been navigated to the target site, the heat source may be deactivated to cause the polymeric member to decrease in temperature and increase in stiffness. The increase in stiffness of the distal portion of the guide wire enhances support provided for devices (e.g., catheters) advanced thereon.

26 Claims, 1 Drawing Sheet

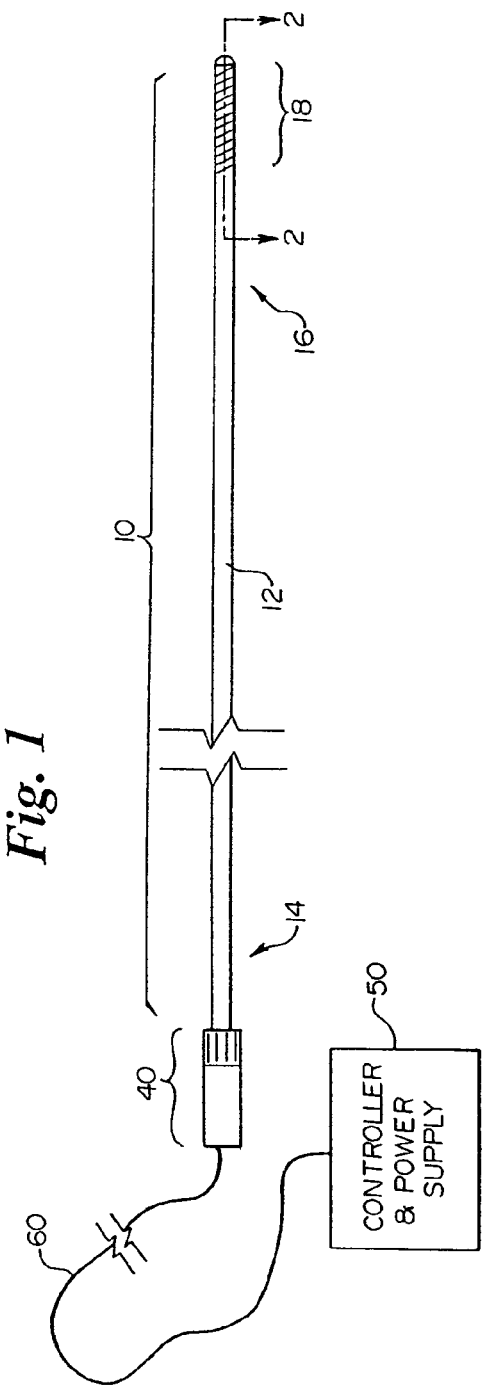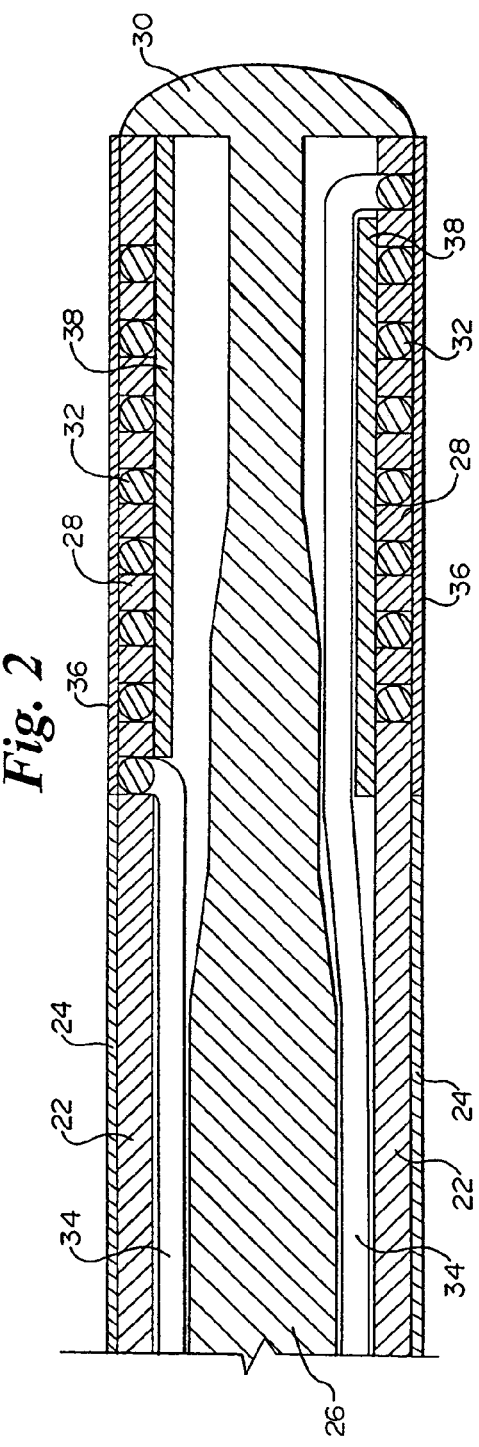

GUIDE WIRE WITH ADJUSTABLE FLEXIBILITY

FIELD OF THE INVENTION

The present invention generally relates to intravascular guide wires. In particular, the present invention relates to intravascular guide wires having adjustable flexibility.

BACKGROUND OF THE INVENTION

Intravascular guide wires are often used to facilitate the delivery of therapeutic and diagnostic devices to remote vascular sites in the human body. In particular, intravascular guide wires are used to navigate through a patient's vasculature from a convenient location outside the patient's body, to a target site inside the patient's body requiring diagnosis and/or therapy. Once access to the target site has been provided by the guide wire, a therapeutic or diagnostic device (e.g., catheter) may then be advanced over the guide wire to the target site, and the desired therapeutic or diagnostic steps may be performed.

To facilitate navigation in tortuous vasculature, it is desirable that the guide wire have a relatively flexible distal end. To provide good support for devices advanced over the guide wire, it is desirable that the guide wire have a relatively stiff distal end. Conventional guide wires typically address these competing needs by establishing a compromise in flexibility and stiffness. However, it would be desirable to have a guide wire that does not compromise these competing needs.

SUMMARY OF THE INVENTION

To address these needs, the present invention provides, in one exemplary embodiment, a guide wire that has a distal portion with adjustable flexibility. In one example, the guide wire includes a distal polymeric member and a heat source. The heat source may be activated by a power supply, which causes the polymeric member to increase in temperature, to thereby increase the flexibility of the distal portion of the guide wire. The polymeric member may comprise a shape memory polymer having a glass transition temperature, wherein the increase in temperature is across the glass transition temperature.

The increase in flexibility of the distal portion of the guide wire enhances the ability of the guide wire to navigate vasculature of varying degrees of tortuosity. After the guide wire has been navigated to the target site, the heat source may be deactivated, which causes the polymeric member to decrease in temperature, to thereby increase the stiffness of the distal portion of the guide wire and provide enhanced support for devices advanced thereon.

BRIEF DESCRIPTION OF THE DRAWINGS

FIG. 1 is a plan view of a guide wire system, including a guide wire, a controller/power source and a coupling/lead therebetween, in accordance with an exemplary embodiment of the present invention; and FIG. 2 is a longitudinal cross-sectional view taken along line 2—2 in FIG. 1, illustrating in detail the distal portion of the guide wire shown in FIG. 1.

DETAILED DESCRIPTION

The following description should be read with reference to the drawings wherein like reference numerals indicate like elements throughout the several views. The detailed description and drawings illustrate embodiments by way of example, not limitation.

Refer now to FIG. 1 which illustrates a guide wire system in accordance with an exemplary embodiment of the present invention. The guide wire system includes a guide wire 10 connected to a controller and power source 50 by a coupling 40 and lead 60.

Guide wire 10 includes an elongate shaft 12 having a proximal portion 14 and a distal portion 16. Distal portion 16 includes a soft atraumatic tip 18. The proximal portion 14 of the shaft 12 is relatively stiff to provide pushability and torquability, and the distal portion 16 has adjustable flexibility to provide trackability in navigating tortuous vasculature and support for devices advanced thereover.

Except as described herein and implicit in the drawings, the guide wire 10 may have conventional dimensions and may be formed of conventional materials using conventional techniques known for intravascular guide wires used to navigate the human vasculature to remote locations including, but not limited to, the neurovasculature, the coronary vasculature, and the peripheral vasculature.

As will be discussed in more detail with reference to FIG. 2, the distal portion 16 of the guide wire 10 includes a heat source that is thermally connected to a polymeric member that increases in flexibility when heated, and increases in stiffness (e.g., returns to its nominal flexibility or stiffness at body temperature) when cooled. Thus, by activating or deactivating the heat source, the flexibility of the polymeric member, and thus the flexibility of the distal portion 16, may be adjusted. For example, the flexibility of the distal portion 16 may be increased by activating the heat source, which enhances the ability of the guide wire 10 to navigate tortuous vasculature to a target site. After the guide wire 10 has been navigated to the desired target site, the heat source may be deactivated to cause the distal portion 16 to increase in stiffness, which enhances guide wire 10 support provided for devices (e.g., catheters) advanced thereon.

To control activation and deactivation of the heat source, a controller/power supply 50 is connected by lead 60 to a coupling 40 which is releasably and rotatably connected to the proximal portion 14 of the guide wire shaft 12. Controller/power supply 50 may comprise a conventional power supply with conventional control circuitry to provide a constant or modulated AC or DC signal. The signal is transmitted by lead 60, which may comprise two (or more) conductors. The conductors in the lead 60 may be connected to leads in the shaft 12 of the guide wire by coupling 40. Coupling 40 may be removable to permit devices such as catheters to be advanced over the proximal end of the guide wire 10. Coupling 40 may also be rotatable to permit the guide wire to be rotated and steered during intravascular navigation.

Refer now to FIG. 2 which illustrates in detail certain aspects of the distal portion 16 of the guide wire 10, which may be in common with certain aspects of the proximal portion 14. As seen in FIG. 2, the shaft 12 includes a hypotube 22 which may comprise, for example, stainless steel or a super elastic metal such as a nickel titanium alloy, Nitinol, MP35N, Inconel, etc. The hypotube 22 may extend from the proximal end of the guide wire shaft 12, and may include an outer sleeve 24 comprising a polymer such as polyurethane. A tapered core wire 26 may extend through the lumen in the hypotube 22, and may comprise stainless steel or a super elastic metal such as a nickel titanium alloy, Nitinol, MP35N, Inconel, etc. The distal end of the hypotube 22 in the region of the distal tip 18 may be helically slotted 28 to enhance flexibility. The distal end of the core wire 26 may be welded to the distal end of the slotted portion 28 of the hypotube 22 to form an atraumatic weld ball 30.

As mentioned previously, the distal portion 16 of the guide wire shaft 12 includes a heat source. In this particular example, the heat source comprises a resistive element 32. Resistive element 32 may comprise a tungsten or steel alloy that may be formed into a coil and heated by electro-resistive heating. Heater coil 32 may be disposed between adjacent turns in the slotted portion 28 of the hypotube 22. The resistive heater coil 32 is connected to insultated leads 34 which may be disposed in the lumen of the hypotube 22 around the core wire 26. Leads 34 are connected to coupling 40, which in turn is connected to controller/power supply 50 via lead 60.

A polymeric outer tube 36 may be disposed about the resistive heater coil 32, and a polymeric inner tube 38 may be provided to support the heater coil 32. The polymeric outer tube 36 and/or the polymeric inner tube 38 may be formed of a polymer that changes in stiffness when heated. For example, the polymeric outer tube 36 and/or the polymeric inner tube 38 may be formed of a polymer that is relatively stiff at temperatures at or below body temperature (37° C. or less) and relatively flexible at temperatures above body temperature. For example, a polymer may be selected with a glass transition temperature ($T_g$) that is above body temperature, such that heating the polymer above $T_g$ results in the distal portion 16 of the guide wire 10 becoming relatively more flexible, and cooling the polymer below $T_g$, even when the guide wire 10 is disposed in the patient's body, results in the distal portion 16 of the guide wire 10 becoming relatively more stiff. In a preferred embodiment, the polymeric outer tube 36 and/or the polymeric inner tube 38 may be formed of a shape memory polymer (SMP) such as a shape memory polyurethane available from Mitsubishi. Other examples of suitable SMPs include polynorbornenes, polycaprolactones and copolymers thereof available from Pnemoscience. Some SMPs, such as polynorbornene, may change flexibility without changing temperature across $T_g$. Such SMPs may be above $T_g$ at room temperature or body temperature, and may exhibit SMP characteristics at or near the melt temperature ($T_m$).

It should be understood that this disclosure is, in many respects, only illustrative. Changes may be made in details, particularly in matters of shape, size, arrangement of parts and order of steps without departing from the scope of the invention. The invention's scope is, of course, defined in the language in which the appended claims are expressed.

What is claimed is:

1. A variable stiffness guide wire, comprising:
   a shaft having a proximal portion and a distal portion, the distal portion having a flexibility;
   a polymeric member disposed on and non-releasably attached to the distal portion of the shaft, the polymeric member having a first flexibility at a first temperature and a second flexibility at a second temperature, wherein the first temperature is less than the second temperature and the first flexibility is less than the second flexibility; and
   a heat source disposed on the distal portion of the shaft, the heat source being in thermal communication with the polymeric member, whereby activation of the heat source causes the polymeric member to rise from the first temperature to the second temperature to thereby change the flexibility of the distal portion of the guide wire while the polymeric member remains attached to the shaft.

2. A variable stiffness guide wire as in claim 1, wherein the polymeric member comprises a shape memory polymer.

3. A variable stiffness guide wire as in claim 2, wherein the shape memory polymer has a glass transition temperature, and wherein the first temperature is below the glass transition temperature.

4. A variable stiffness guide wire as in claim 3, wherein the second temperature is above the glass transition temperature.

5. A variable stiffness guide wire as in claim 1, wherein the heat source comprises a resistive heating element.

6. A variable stiffness guide wire as in claim 5, wherein the distal portion of the shaft includes a tip portion.

7. A variable stiffness guide wire as in claim 6, wherein the tip portion includes the polymeric member and resistive heating element.

8. A variable stiffness guide wire as in claim 7, wherein the polymeric member comprises a tube.

9. A variable stiffness guide wire as in claim 8, wherein the resistive heating element comprises a coiled wire.

10. A variable stiffness guide wire as in claim 9, further comprising one or more lead wires connected to and extending proximally from the coiled wire.

11. A variable stiffness guide wire as in claim 10, wherein the polymeric tube is disposed on the coiled wire.

12. A variable stiffness guide wire as in claim 11, wherein a core wire extends through the tip portion.

13. A variable stiffness guide wire as in claim 12, wherein the proximal portion of the shaft includes a hypotube.

14. A variable stiffness guide wire as in claim 13, wherein the distal portion of the shaft includes a slotted hypotube.

15. A variable stiffness guide wire as in claim 14, wherein the coiled wire is disposed in the slots of the slotted hypotube.

16. A variable stiffness guide wire, comprising:
    a shaft including a proximal portion and a distal portion having a flexibility;
    a polymeric member disposed on and non-releasably attached to the distal portion of the shaft;
    a heat source in thermal communication with the polymeric member, whereby activation of the heat source causes the polymeric member to change the flexibility of the distal portion of the shaft;
    wherein the heat source comprises a resistive heating element;
    wherein the distal portion of the shaft includes a tip portion;
    wherein the tip portion includes the polymeric member and resistive heating element;
    wherein the polymeric member comprises a tube;
    wherein the resistive heating element comprises a coiled wire;
    further comprising one or more lead wires connected to and extending proximally from the coiled wire;
    wherein the polymeric tube is disposed on the coiled wire; and
    wherein a core wire extends through the tip portion.

17. A variable stiffness guide wire as in claim 16, wherein the proximal portion of the shaft includes a hypotube.

18. A variable stiffness guide wire as in claim 17, wherein the distal portion of the shaft includes a slotted hypotube.

19. A variable stiffness guide wire as in claim 18, wherein the coiled wire is disposed in the slots of the slotted hypotube.

20. A method of using a variable stiffness guide wire, comprising the steps of:
providing a guide wire including a distal portion having a flexibility, a shaft, a distal polymeric member non-releasably attached to the shaft, and a heat source in thermal communication with the polymeric member;
changing the flexibility of the distal portion of the guide wire by activating or deactivating the heat source;
wherein the flexibility changing step comprises activating the heat source to increase the flexibility of the distal portion of the guide wire, the method further comprising the step of navigating the guide wire through a patient's vasculature to a target site; and
further comprising: the step of deactivating the heat source to decrease the flexibility of the distal portion of the guide wire.

21. A method of using a variable stiffness guide wire as in claim 20, further comprising the step of advancing a device over the guide wire to the target site.

22. A variable stiffness guide wire, comprising:
a shaft including a proximal portion and a distal portion having a flexibility;
a polymeric member disposed on and non-releasably attached to the distal portion of the shaft;
a heat source in thermal communication with the polymeric member, whereby activation of the heat source causes the polymeric member to change the flexibility of the distal portion of the shaft;
wherein the polymeric member comprises a shape memory polymer;
wherein activation of the heat source causes the shape memory polymer to change temperature; and
wherein the shape memory polymer has a glass transition temperature, and wherein the change in temperature is across the glass transition temperature.

23. A variable stiffness guide wire, comprising:
a shaft including a proximal portion and a distal portion having a flexibility;
a polymeric member disposed on and non-releasably attached to the distal portion of the shaft;
a heat source in thermal communication with the polymeric member, whereby activation of the heat source causes the polymeric member to change the flexibility of the distal portion of the shaft;
wherein the polymeric member comprises a shape memory polymer;
wherein activation of the heat source causes the shape memory polymer to change temperature; and
wherein the shape memory polymer has a glass transition temperature, and wherein the change in temperature is near the melt temperature.

24. A method of using a variable stiffness guide wire, comprising:
providing a guide wire including a distal portion having a flexibility, a shaft, a distal polymeric member non-releasably attached to the shaft, and a heat source in thermal communication with the polymeric member;
changing the flexibility of the distal portion of the guide wire by activating or deactivating the heat source; and
wherein the polymeric member comprises a shape memory polymer having a glass transition temperature, and wherein the flexibility changing step comprises heating the polymeric member near the melt temperature.

25. A method of using a variable stiffness guide wire, comprising:
providing a guide wire including a distal portion having a flexibility, a shaft, a distal polymeric member non-releasably attached to the shaft, and a heat source in thermal communication with the polymeric member;
changing the flexibility of the distal portion of the guide wire by activating or deactivating the heat source; and
wherein the polymeric member comprises a shape memory polymer having a glass transition temperature, and wherein the flexibility changing step comprises heating the polymeric member above the glass transition temperature.

26. A variable stiffness guide wire, comprising:
a hypotube having a proximal portion and a distal portion, the distal portion having a flexibility;
a polymeric member disposed on and attached to the distal portion of the hypotube, the polymeric member having a first flexibility at a first temperature and a second flexibility at a second temperature, wherein the first temperature is less than the second temperature and the first flexibility is less than the second flexibility; and
a heat source disposed on the distal portion of the hypotube, the heat source being in thermal communication wit the polymeric member, whereby activation of the heat source causes the polymeric member to rise from the first temperature to the second temperature to thereby change the flexibility of the distal portion of the guide wire.

* * * * *

UNITED STATES PATENT AND TRADEMARK OFFICE
CERTIFICATE OF CORRECTION

| | |
|---|---|
| PATENT NO. | : 7,018,346 B2 |
| APPLICATION NO. | : 10/025428 |
| DATED | : March 28, 2006 |
| INVENTOR(S) | : Stephen Griffin et al. |

It is certified that error appears in the above-identified patent and that said Letters Patent is hereby corrected as shown below:

Column 5
Line 17, delete the colon " : "

Column 6
Line 42, delete "wit", and insert therefor -- with --

Signed and Sealed this

Eighth Day of August, 2006

JON W. DUDAS
*Director of the United States Patent and Trademark Office*